(12) United States Patent
Maeda (10) Patent No.: US 10,374,259 B2
(45) Date of Patent: Aug. 6, 2019

(54) HYDROFLUOROETHER COMPOUND, NONAQUEOUS ELECTROLYTE SOLUTION AND LITHIUM ION SECONDARY BATTERY

(71) Applicant: NEC Corporation, Tokyo (JP)

(72) Inventor: Katsumi Maeda, Tokyo (JP)

(73) Assignee: NEC Corporation, Tokyo (JP)

( * ) Notice: Subject to any disclaimer, the term of this patent is extended or adjusted under 35 U.S.C. 154(b) by 22 days.

(21) Appl. No.: 15/560,807

(22) PCT Filed: Mar. 2, 2016

(86) PCT No.: PCT/JP2016/056466
§ 371 (c)(1),
(2) Date: Sep. 22, 2017

(87) PCT Pub. No.: WO2016/152425
PCT Pub. Date: Sep. 29, 2016

(65) Prior Publication Data
US 2018/0115020 A1    Apr. 26, 2018

(30) Foreign Application Priority Data
Mar. 25, 2015    (JP) .................. 2015-062654

(51) Int. Cl.
*H01M 10/0569*    (2010.01)
*C07C 41/22*    (2006.01)
(Continued)

(52) U.S. Cl.
CPC ......... *H01M 10/0569* (2013.01); *C07C 41/22* (2013.01); *C07C 43/126* (2013.01);
(Continued)

(58) Field of Classification Search
CPC .......... H01M 4/38; H01M 4/48; H01M 4/505; H01M 4/525; H01M 4/587;
(Continued)

(56) References Cited

U.S. PATENT DOCUMENTS 5,476,974 A    12/1995   Moore et al.
5,994,599 A    11/1999   Petrov
(Continued)

FOREIGN PATENT DOCUMENTS

CA    2 719 405 A1    11/2009
EP    2 270 917 A1    1/2011
(Continued)

OTHER PUBLICATIONS

International Search Report corresponding to PCT/JP2016/056466, dated May 31, 2016 (5 pages).
(Continued)

*Primary Examiner* — Amanda C. Walke
(74) *Attorney, Agent, or Firm* — Wilmer Cutler Pickering Hale and Dorr LLP (57) ABSTRACT

A nonaqueous electrolyte solution including a hydrofluoroether compound represented by the following formula (1):

[Formula 1]

$$CF_3CF_2CF_2OCHFCF_2OR^1 \qquad (1)$$

wherein $R^1$ represents a difluoromethyl group, a 2,2-difluoroethyl group, a 2,2,2-trifluoroethyl group, a 2,2,3,3,3-pentafluoropropyl group, a 2,2,3,3-tetrafluoropropyl group, a 1,1,1,3,3,3-hexafluoroisopropyl group, a 2,2,3,3,4,4,4-heptafluorobutyl group, a 2,2,3,3,4,4-hexafluorobutyl group, or a 2,2,3,3,4,4,5,5-octafluoropentyl group.

12 Claims, 1 Drawing Sheet

(51) Int. Cl.
| | |
|---|---|
| *H01M 4/38* | (2006.01) |
| *H01M 4/48* | (2010.01) |
| *H01M 10/052* | (2010.01) |
| *H01M 10/0567* | (2010.01) |
| *C07C 43/12* | (2006.01) |
| *H01M 4/505* | (2010.01) |
| *H01M 4/525* | (2010.01) |
| *H01M 4/587* | (2010.01) |
| *H01M 10/0525* | (2010.01) |
| *H01M 10/42* | (2006.01) |

(52) U.S. Cl.
CPC ............... *H01M 4/38* (2013.01); *H01M 4/48* (2013.01); *H01M 4/505* (2013.01); *H01M 4/525* (2013.01); *H01M 4/587* (2013.01); *H01M 10/052* (2013.01); *H01M 10/0525* (2013.01); *H01M 10/0567* (2013.01); *H01M 10/4235* (2013.01); *H01M 2300/004* (2013.01); *H01M 2300/0034* (2013.01)

(58) Field of Classification Search
CPC ........... H01M 10/0569; H01M 10/052; H01M 10/0525; C07C 43/126; C07C 41/22
USPC .................................. 429/332; 570/136, 142
See application file for complete search history.

(56) References Cited

U.S. PATENT DOCUMENTS

| | | | | |
|---|---|---|---|---|
| 7,691,282 | B2* | 4/2010 | Flynn .................... | C07C 43/126 134/42 |
| 7,790,312 | B2* | 9/2010 | Costello ............ | H01M 10/0569 429/188 |
| 2007/0051916 | A1 | 3/2007 | Flynn et al. | |
| 2007/0054186 | A1 | 3/2007 | Costello et al. | |
| 2011/0020700 | A1 | 1/2011 | Iwaya | |
| 2012/0214073 | A1* | 8/2012 | Iwaya ............... | H01M 10/0525 429/338 |
| 2016/0087307 | A1* | 3/2016 | Burkhardt ......... | H01M 10/0567 429/163 |

FOREIGN PATENT DOCUMENTS

| | | |
|---|---|---|
| JP | 2001-023691 A | 1/2001 |
| JP | 2004-203889 A | 7/2004 |
| JP | 2004-363031 A | 12/2004 |
| JP | 2006-049037 A | 2/2006 |
| JP | 2006-199625 A | 8/2006 |
| JP | 2009-507840 A | 2/2009 |
| JP | 2009-508304 A | 2/2009 |
| JP | 2010-040382 A | 2/2010 |
| JP | 2010-238510 A | 10/2010 |
| JP | 2013-254605 A | 12/2013 |
| JP | 2014-022276 A | 2/2014 |
| WO | WO-2009/133899 A1 | 11/2009 |
| WO | WO-2012/141301 A1 | 10/2012 |

OTHER PUBLICATIONS

Zhang, Journal of Power Sources, vol. 162, (2006), "A review on electrolyte additives for lithium-ion batteries," pp. 1379-1394.

Petrov, Journal of Fluorine Chemistry, vol. 112, (2001),"New synthesis of hydrofluoroethers," pp. 117-121.

Chi et al., Bull. Korean Chem. Soc., vol. 20, No. 2, (1999), "A Facile Synthesis of Partly-fluorinated Ethers Using Perfluoropropoxyethylene and Aliphatic Alcohols," pp. 220-222.

* cited by examiner

HYDROFLUOROETHER COMPOUND, NONAQUEOUS ELECTROLYTE SOLUTION AND LITHIUM ION SECONDARY BATTERY

CROSS-REFERENCE TO RELATED APPLICATIONS

This application is a national stage application of International Application No. PCT/JP2016/056466 entitled "HYDROFLUOROETHER COMPOUND, NONAQUEOUS ELECTROLYTE SOLUTION AND LITHIUM ION SECONDARY BATTERY," filed on Mar. 2, 2016, which claims the benefit of the priority of Japanese Patent Application No. 2015-062654, filed on Mar. 25, 2015, the disclosures of each of which are hereby incorporated by reference in their entirety.

TECHNICAL FIELD

The present invention relates to a hydrofluoroether compound, a nonaqueous electrolyte solution containing the hydrofluoroether compound, and a lithium ion secondary battery using the nonaqueous electrolyte solution.

BACKGROUND ART

Nonaqueous electrolyte secondary batteries such as lithium ion secondary batteries have already been put into practical use as batteries for small-size electronic devices such as laptop computers and cell phones, or the like, thanks to such advantages as their high energy density, low self-discharge, excellent long-term reliability and the like. Further, in recent years, utilization of the nonaqueous electrolyte secondary batteries has expanded to storage batteries for electric cars, household storage batteries and power storage batteries.

The lithium ion secondary batteries are constituted of a positive electrode containing mainly a positive electrode active substance, a negative electrode having, as its main component, a material capable of occluding and releasing lithium ions, and a nonaqueous electrolyte solution. As the positive electrode active substance to be used for the positive electrode, a lithium metal oxide such as $LiCoO_2$, $LiMnO_2$, $LiNiO_2$, $LiFePO_4$ or $LiMn_2O_4$ is used, for example.

Further, as the negative electrode active substance to be used for the negative electrode, metallic lithium, or silicon, an oxide such as silicon oxide or a carbonaceous material capable of occluding and releasing lithium ions are used. Lithium ion secondary batteries particularly using graphite (artificial graphite, natural graphite) or a carbonaceous material such as coke capable of occluding and releasing lithium ions have already been put into practical use.

On the other hand, as the nonaqueous electrolyte solution, one in which a lithium salt such as $LiPF_6$, $LiBF_4$, $LiN(SO_2F)_2$, $LiN(SO_2CF_3)_2$, $LiN(SO_2C_2F_5)_2$ or lithium bis(oxalate)borate $(LiB(C_2O_4)_2)$ is added to a mixed solvent of a cyclic carbonate solvent such as ethylene carbonate or propylene carbonate and a chain carbonate solvent such as dimethyl carbonate, diethyl carbonate or ethyl methyl carbonate is used, for example.

In secondary batteries using such a nonaqueous electrolyte solution, for example, on the electrode surface of the negative electrode, a solvent in the electrolyte solution causes a reductive decomposition, whereby the decomposition product deposits on the negative electrode surface to increase the resistance, and gases generated by the decomposition of the solvent bulge the battery. Further on the electrode surface of the positive electrode, the solvent causes an oxidative decomposition, whereby the decomposition product deposits on the positive electrode surface to increases the resistance, and gases generated by the decomposition of the solvent bulge the battery. Consequently, decreases in the storage characteristics of the batteries and decreases in the cycle characteristics of the secondary batteries occur to arise a problem of decreases in the battery characteristics.

In order to prevent occurrence of these problems, a compound having a function of forming a protective coating, for example, vinylene carbonate, fluoroethylene carbonate or maleic anhydride is added to the nonaqueous electrolyte solution. Specifically, it is known that the decomposition of the compound added in the electrolyte solution is intentionally promoted on an electrode active substance surface during the initial charge time, and its decomposition product forms a protective coating having a protection function to prevent another decomposition of the solvent, that is, forms an SEI (Solid Electrolyte Interface). Then, it is reported that formation of the protective coating suitably suppresses the chemical reaction and the decomposition of the solvent on an electrode surface and consequently to exhibit an effect of maintaining battery characteristics of a secondary battery (Non Patent Literature 1). These additives are generally considered, however, to form an SEI on the negative electrode surface, and are insufficient to suppress gas generation and the like due to the oxidative decomposition of the solvent on the positive electrode.

Further, recently, in order to realize secondary batteries having a high energy density, use of positive electrodes having a high potential has been studied. For example, it is stated in Patent Literature 1 (JP2013-254605A) that a lithium metal composite oxide having a layered rock salt structure represented by $Li_{1.19}Mn_{0.52}Fe_{0.22}O_{1.98}$ is used for a positive electrode active substance; and in Patent Literature 2 (WO2012/141301) that a lithium metal composite oxide represented by $LiNi_{0.5}Mn_{1.5}O_4$ is used for a positive electrode active substance. Since such lithium ion secondary batteries using positive electrodes having a high potential have higher voltages (4.5 V or more) than voltages of conventional common lithium secondary batteries (3.5 to 4.2 V), gas generation due to the oxidative decomposition of solvents on their positive electrodes is liable to occur.

On the other hand, as a method for suppressing the oxidative decomposition of a solvent in an electrolyte solution, an attempt is made in which the electrolyte solution is made to contain a fluorine-containing ether (Patent Literature 3: JP2004-363031A).

CITATION LIST

Patent Literature

Patent Literature 1: JP2013-254605A
Patent Literature 2: WO2012/141301
Patent Literature 3: JP2004-363031A

Non Patent Literature

Non Patent Literature 1: Journal. Power Sources, vol. 162, pp. 1379-1394 (2006)

SUMMARY OF INVENTION

Technical Problem

The nonaqueous electrolyte solution containing a fluorine-containing ether used in the related art described in Patent Literature 3 and the like, however, cannot yet be said to be sufficient in that gas generation is suppressed in lithium ion secondary batteries using positive electrodes having a high potential of 4.5 V or more, and then, a further improvement in battery characteristics is demanded.

An object of the present invention is to solve the above problem, and to provide a lithium ion secondary battery improved in characteristics, and a nonaqueous electrolyte solution and a nonaqueous solvent suitable for the lithium ion secondary battery.

Solution to Problem

According to one aspect of the present invention, there is provided a nonaqueous electrolyte solution for a lithium ion secondary battery containing a hydrofluoroether compound represented by the following formula (1).

[Formula 1]

$$CF_3CF_2CF_2OCHFCF_2OR^1 \qquad (1)$$

In the formula, $R^1$ represents a difluoromethyl group, a 2,2-difluoroethyl group, a 2,2,2-trifluoroethyl group, a 2,2,3,3,3-pentafluoropropyl group, a 2,2,3,3-tetrafluoropropyl group, a 1,1,1,3,3,3-hexafluoroisopropyl group, a 2,2,3,3,4,4,4-heptafluorobutyl group, a 2,2,3,3,4,4-hexafluorobutyl group, or a 2,2,3,3,4,4,5,5-octafluoropentyl group.

According to another aspect of the present invention, there is provided a lithium ion secondary battery comprising a positive electrode containing a positive electrode active substance material capable of occluding and releasing lithium ions, a negative electrode containing a negative electrode active substance material capable of occluding and releasing lithium ions, and the above nonaqueous electrolyte solution.

According to another aspect of the present invention, there is provided a hydrofluoroether compound represented by the following formula (1).

[Formula 2]

$$CF_3CF_2CF_2OCHFCF_2OR^1 \qquad (1)$$

In the formula, $R^1$ represents a difluoromethyl group, a 2,2-difluoroethyl group, a 2,2,3,3,3-pentafluoropropyl group, a 2,2,3,3-tetrafluoropropyl group, a 1,1,1,3,3,3-hexafluoroisopropyl group, a 2,2,3,3,4,4,4-heptafluorobutyl group, a 2,2,3,3,4,4-hexafluorobutyl group, or a 2,2,3,3,4,4,5,5-octafluoropentyl group.

Advantageous Effects of Invention

According to exemplary embodiments, the gas generation of a lithium ion secondary battery can be suppressed, whereby there can be provided a lithium ion secondary battery improved in the battery characteristics and having a high energy density, and there can be provided a nonaqueous electrolyte solution and a hydrofluoroether compound suitable for the lithium ion secondary battery.

DESCRIPTION OF EMBODIMENTS

As a result of exhaustive studies to solve the above-mentioned problem, the present inventors have found that by using a diether-type hydrofluoroether compound having a specific structure for a nonaqueous electrolyte solution, the gas generation of a lithium ion secondary battery can be suppressed and excellent battery characteristics can be realized, and this finding has led to the completion of the present invention.

That is, a nonaqueous electrolyte solution according to one exemplary embodiment comprises the above hydrofluoroether compound represented by the formula (1).

Further, a lithium ion secondary battery according to another exemplary embodiment comprises a positive electrode containing a positive electrode active substance material capable of occluding and releasing lithium ions, a negative electrode containing a negative electrode active substance material capable of occluding and releasing lithium ions, and the above nonaqueous electrolyte solution.

Further, a hydrofluoroether compound according to another exemplary embodiment is represented by the formula (1). According to this exemplary embodiment, there can be provided a nonaqueous solvent containing the hydrofluoroether compound suitable for a lithium ion secondary battery.

By making the hydrofluoroether compound represented by the formula (1) to be contained in a nonaqueous electrolyte solution, the chemical reaction and the decomposition of the electrolyte solution on the positive electrode surface are suitably suppressed and the gas generation can be thereby suppressed, and there can be attained an effect of holding the long-term reliability and the life of the secondary battery. Thereby, there can be provided the lithium ion secondary battery high in the capacity, high in the energy density and excellent in the stability of the charge and discharge cycle.

Hereinafter, there will be described in detail a hydrofluoroether compound suitable for a nonaqueous electrolyte solution according to the exemplary embodiment, the nonaqueous electrolyte solution containing the hydrofluoroether compound and a lithium ion secondary battery using the nonaqueous electrolyte solution.

(Hydrofluoroether Compound)

A hydrofluoroether compound usable for a nonaqueous electrolyte solution according to the exemplary embodiment is a diether type compound represented by the formula (1).

[Formula 3]

$$CF_3CF_2CF_2OCHFCF_2OR^1 \qquad (1)$$

In the formula (1), $R^1$ is a group selected from the group consisting of a difluoromethyl group, a 2,2-difluoroethyl group, a 2,2,2-trifluoroethyl group, a 2,2,3,3,3-pentafluoropropyl group, a 2,2,3,3-tetrafluoropropyl group, a 1,1,1,3,3,3-hexafluoroisopropyl group, a 2,2,3,3,4,4,4-heptafluorobutyl group, a 2,2,3,3,4,4-hexafluorobutyl group, or a 2,2,3,3,4,4,5,5-octafluoropentyl group. Among these, from the viewpoint of the solubility of an electrolyte (for example, a Li salt such as $LiPF_6$ or $LiBF_4$) in the nonaqueous electrolyte solution, $R^1$ is more preferably a difluoromethyl group, a 2,2-difluoroethyl group, a 2,2,3,3-tetrafluoropropyl group, a 2,2,3,3,4,4-hexafluorobutyl group and a 2,2,3,3,4,4,5,5-octafluoro pentyl group, whose terminal structures are a difluoromethyl structure (—$CF_2H$). Specifically, when a hydrofluoroether compound represented by the formula (1) in which $R^1$ is a difluoromethyl group, a 2,2-difluoroethyl group, a 2,2,3,3-tetrafluoropropyl group, a 2,2,3,3,4,4-hexafluorobutyl group or a 2,2,3,3,4,4,5,5-octafluoropentyl group is used for the nonaqueous electrolyte solution, also in the case where the content of the hydrofluoroether compound in the whole of nonaqueous electrolyte solution is 20% by volume or more, the electrolyte such as $LiPF_6$, even in a concentration of 1 mol/L, can be homogeneously dissolved.

Chemical structural formulae of specific examples of the hydrofluoroether compound represented by the above formula (1) are shown in Table 1.

TABLE 1

| compound | Chemical structural formula |
|---|---|
| HFE-1 | $CF_3CF_2CF_2OCHFCF_2OCH_2CHF_2$ |
| HFE-2 | $CF_3CF_2CF_2OCHFCF_2OCH_2CF_2CHF_2$ |
| HFE-3 | $CF_3CF_2CF_2OCHFCF_2OCH_2CF_3$ |
| HFE-4 | $CF_3CF_2CF_2OCHFCF_2OCH_2CF_2CF_3$ |
| HFE-5 | $CF_3CF_2CF_2OCHFCF_2OCH(CF_3)_2$ |
| HFE-6 | $CF_3CF_2CF_2OCHFCF_2OCHF_2$ |
| HFE-7 | $CF_3CF_2CF_2OCHFCF_2OCH_2CF_2CF_2CHF_2$ |
| HFE-8 | $CF_3CF_2CF_2OCHFCF_2OCH_2CF_2CF_2CF_3$ |
| HFE-9 | $CF_3CF_2CF_2OCHFCF_2OCH_2CF_2CF_2CF_2CHF_2$ |

These compounds can be produced by common methods, and for example, HFE-1 of the above hydrofluoroether compounds can be produced by the following step according to a method described in Bull. Korean Chem. Soc., Vol. 30, No. 2, pp. 220-222(1999).

[Formula 4]

HFE-1

By reacting perfluoropropoxyethylene with 2,2-difluoroethanol in tetrahydrofuran in the presence of potassium hydroxide, a target hydrofluoroether compound (HFE-1) can be obtained.

(Lithium Ion Secondary Battery)

A lithium ion secondary battery according to the exemplary embodiment can have a constitution comprising mainly a positive electrode, a negative electrode, a nonaqueous electrolyte solution (containing a nonaqueous solvent containing a hydrofluoroether compound represented by the formula (1), and an electrolyte salt dissolved in the nonaqueous solvent), and a separator disposed between the positive electrode and the negative electrode. Hereinafter, there will be described each constituent suitable for the lithium ion secondary battery according to the exemplary embodiment.

<1. Nonaqueous Electrolyte Solution>

The nonaqueous electrolyte solution for the lithium ion secondary battery according to the exemplary embodiment comprises mainly a nonaqueous solvent and an electrolyte salt, and the nonaqueous solvent contains at least one of hydrofluoroether compounds represented by the formula (1). Further, the nonaqueous solvent can contain other nonaqueous solvents (nonaqueous organic solvents) other than the hydrofluoroether represented by the formula (1). The other nonaqueous solvents can appropriately be selected from among ones usually used, and can be used singly or as a mixture of two or more. Examples of the other nonaqueous solvents include cyclic carbonates, chain carbonates, chain esters, lactones, ethers, fluorinated ethers, sulfones, nitriles, phosphate esters and fluorine-containing phosphate esters.

Specific examples of the cyclic carbonate include propylene carbonate, ethylene carbonate, fluoroethylene carbonate, butylene carbonate, vinylene carbonate and vinyl ethylene carbonate.

Specific examples of the chain carbonate include dimethyl carbonate, diethyl carbonate, ethyl methyl carbonate, dipropyl carbonate, dibutyl carbonate, methyl propyl carbonate, methyl isopropyl carbonate, methyl butyl carbonate, fluoromethyl methyl carbonate, 2-fluoroethyl methyl carbonate, ethyl-(2-fluoroethyl) carbonate, ethyl-(2,2-difluoroethyl) carbonate, bis(2-fluoroethyl) carbonate and ethyl-(2,2,2-trifluoroethyl) carbonate.

Specific examples of the chain ester include carboxylate esters such as methyl formate, methyl acetate, methyl propionate, ethyl propionate, methyl pivalate, ethyl pivalate, 3,3,3-trifluoromethyl propionate, methyl difluoroacetate, ethyl difluoroacetate and ethyl heptafluorobutyrate.

Specific examples of the lactone include γ-butyrolactone, δ-valerolactone and α-methyl-γ-butyrolactone.

Specific examples of the ether include tetrahydrofuran, 2-methyltetrahydrofuran, 1,3-dioxolane, 1,3-dioxane, 1,4-dioxane, 1,2-dimethoxyethane, 1,2-diethoxyethane and 1,2-dibutoxyethane.

The fluorine-containing ether includes fluorine-containing ethers represented by the following formula (2), and specific examples thereof include 1,1,2,2-tetrafluoroethyl 2,2,3,3-tetrafluoropropyl ether, 1H,1H,5H-octafluoropentyl 1,1,2,2-tetrafluoroethyl ether, 1H,1H,2H-pentafluorodiisopropyl ether and 1H,1H,2'H,3H-decafluorodiisopropyl ether.

[Formula 5]

In the formula, $R^2$ and $R^3$ are each independently an alkyl group or a fluorine-containing alkyl group, and at least one thereof is a fluorine-containing alkyl group. The alkyl group or the fluorine-containing alkyl group contains preferably 1 to 7 carbon atoms, and more preferably 2 to 5 carbon atoms.

Specific examples of the sulfone include sulfolane, 3-methylsulfolane and 2,4-dimethylsulfolane.

Specific examples of the nitrile include acetonitrile, propionitrile, succinonitrile, glutaronitrile and adiponitrile.

Specific examples of the phosphate ester include trimethyl phosphate, triethyl phosphate, tributyl phosphate and trioctyl phosphate.

The fluorine-containing phosphate ester include fluorine-containing phosphate esters represented by the formula (3), and specific examples thereof include tris(2,2,2-trifluoroethyl) phosphate, tris(trifluoromethyl) phosphate and tris(2,2,3,3-tetrafluoropropyl) phosphate.

[Formula 6]

In the formula, $R^4$, $R^5$ and $R^6$ are each independently an alkyl group or a fluorine-containing alkyl group, and at least one thereof is a fluorine-containing alkyl group. The alkyl group or the fluorine-containing alkyl group contains preferably 1 to 5 carbon atoms, and more preferably 1 to 3 carbon atoms.

By adding the fluorine-containing ether such as a compound represented by the formula (2) and the phosphate ester such as a compound represented by the formula (3) to the nonaqueous electrolyte solution, the effects of suppressing the amount of gas generated and improving the cycle characteristics can be anticipated.

As the nonaqueous solvent of the nonaqueous electrolyte solution according to the exemplary embodiment, a nonaqueous solvent containing a hydrofluoroether represented by the formula (1) and other nonaqueous solvents can be used.

The content of the hydrofluoroether represented by the formula (1) in the nonaqueous solvent of the nonaqueous electrolyte solution according to the exemplary embodiment is, from the viewpoint of suppression of the gas generation and the battery characteristics, preferably 1% by volume or more and 60% by volume or less, and more preferably 3% by volume or more and 50% by volume or less.

The nonaqueous solvent of the nonaqueous electrolyte solution according to the exemplary embodiment is, in order to achieve excellent battery characteristics, more preferably a nonaqueous solvent containing at least the cyclic carbonate and/or chain carbonate as the other nonaqueous solvents other than the hydrofluoroether compound represented by the formula (1), and the other nonaqueous solvents preferably contain at least the cyclic carbonate. By adding the cyclic carbonate, the ionic conductivity of the nonaqueous electrolyte solution can be raised. The content of the cyclic carbonate contained in the nonaqueous electrolyte solution is not especially limited, but is, from the viewpoint of the ionic conductivity, the viscosity and the like of the nonaqueous electrolyte solution, preferably 5% by volume or more, more preferably 7% by volume or more and still more preferably 10% by volume or more, and preferably 70% by volume or less, more preferably 60% by volume or less and still more preferably 50% by volume or less in the nonaqueous solvent.

Specific examples of the electrolyte salt contained in the nonaqueous electrolyte solution according to the exemplary embodiment include, but not limited to the following examples, lithium salts such as $LiPF_6$, $LiBF_4$, $LiClO_4$, $LiN(SO_2F)_2$, $LiN(SO_2CF_3)_2$, $LiN(SO_2C_2F_5)_2$, $CF_3SO_3Li$, $C_4F_9SO_3Li$, $LiAsF_6$, $LiAlCl_4$, $LiSbF_6$, $LiPF_4(CF_3)_2$, $LiPF_3(C_2F_5)_3$, $LiPF_3(CF_3)_3$, $(CF_2)_2(SO_2)_2NLi$, $(CF_2)_3(SO_2)_2Li$, lithium bis(oxalato)borate and lithium oxalatodifluoroborate. Among these, preferable are $LiPF_6$, $LiBF_4$, $LiN(SO_2F)_2$, $LiN(SO_2CF_3)_2$ and $LiN(SO_2C_2F_5)_2$. These electrolyte salts can be used singly or in combinations of two or more.

The concentration of the electrolyte salt dissolved in the nonaqueous solvent in the nonaqueous electrolyte solution is preferably 0.1 to 3 M (mol/L), and more preferably 0.5 to 2 M. When the concentration of the electrolyte salt is 0.1 mol/L or more, a more sufficient ionic conductivity can be attained; and when the concentration of the electrolyte salt is 3 mol/L or less, the rise in the viscosity of the electrolyte solution is suppressed and a more sufficient ionic mobility and impregnatability can be attained.

The nonaqueous electrolyte solution can also optionally contain known additive compounds for nonaqueous electrolyte solutions as other components. Examples of the additive compounds include vinylene carbonate, fluoroethylene carbonate, maleic anhydride, ethylene sulfite, borate ester, 1,3-propanesultone and 1,5,2,4-dioxadithiane-2,2,4,4-tetraoxide. These other components may be used singly or concurrently in two or more.

<2. Positive Electrode>

As the positive electrode of the lithium ion secondary battery according to the exemplary embodiment, one in which a positive electrode active substance layer containing a positive electrode active substance and a binder for the positive electrode is formed so as to cover on a positive electrode current collector can be used, for example. The binder binds the positive electrode active substance and the current collector, and the positive electrode active substances.

As the positive electrode active substance, a composite metal oxide containing a transition metal such as cobalt, manganese or nickel, and lithium can be used. Such a lithium composite metal oxide specifically includes $LiMnO_2$, $Li_xMn_2O_4$ (0<x<2), $Li_2MnO_3$—$LiMO_2$ solid solutions (M=Co, Ni or the like), $LiCoO_2$, $LiNiO_2$, $LiCo_{1-x}Ni_xO_2$ (0.01<x<1), $LiNi_{1/2}Mn_{3/2}O_4$ and $LiNi_{1/3}Co_{1/3}Mn_{1/3}O_2$. Further, ones having Li in an excessive amount to their stoichiometric compositions, and the like are included in these lithium composite metal oxides.

Further in order to improve the cycle characteristics and the safety, and enable the use at a high charge potential, a part of the lithium composite metal oxide may be substituted with another element. For example, a part of cobalt, manganese and nickel can be substituted with at least one or more elements of Sn, Mg, Fe, Ti, Al, Zr, Cr, V, Ga, Zn, Cu, Bi, Mo, La and the like; a part of oxygen can be substituted with S or F; or the positive electrode surface can be covered with a compound containing these elements.

As the positive electrode active substance, a lithium-containing olivine-type phosphate salt ($LiMPO_4$: M is Fe, Mn, Ni, Mg, Co or the like) can also be used. Specific examples thereof include $LiCoPO_4$, $LiMnPO_4$, $LiNiPO_4$ and $LiFePO_4$.

Examples of specific compositions of the lithium metal composite oxides suitable for the positive electrode of the lithium ion secondary battery according to the exemplary embodiment include $Li_{1.2}Mn_{0.4}Ni_{0.4}O_2$, $Li_{1.19}Mn_{0.52}Fe_{0.22}O_{1.98}$, $Li_{1.21}Mn_{0.46}Fe_{0.15}Ni_{0.15}O_{2.0}$, $LiMn_{1.5}Ni_{0.5}O_4$, $Li_{1.2}Mn_{0.4}Fe_{0.4}O_{2.0}$, $Li_{1.21}Mn_{0.4}Fe_{0.2}Ni_{0.2}O_{2.0}$, $Li_{1.26}Mn_{0.37}Ni_{0.22}Ti_{0.15}O_{2.0}$, $LiMn_{1.37}Ni_{0.5}Ti_{0.13}O_{4.0}$, $Li_{1.2}Mn_{0.56}Ni_{0.17}Co_{0.07}O_{2.0}$, $Li_{1.2}Mn_{0.54}Ni_{0.13}Co_{0.13}O_{2.0}$, $Li_{1.2}Mn_{0.56}Ni_{0.17}Co_{0.07}O_{2.0}$, $LiNi_{0.8}Co_{0.15}Al_{0.05}O_{2.0}$, $LiNi_{0.5}Mn_{1.48}Al_{0.02}O_{4.0}$, $LiNi_{0.5}Mn_{1.45}Al_{0.05}O_{3.9}F_{0.05}$ and $LiNi_{0.4}Co_{0.2}Mn_{1.25}Ti_{0.15}O_{4.0}$.

Synthesis methods of the lithium metal composite oxides represented by the above chemical formulae are not especially limited, and usual synthesis methods of oxides can be applied.

The positive electrode active substance can be used singly or in combinations of two or more.

To the positive electrode active substance layer containing the positive electrode active substance, a conductive auxiliary agent may be added for the purpose of reducing the impedance. The conductive auxiliary agent specifically includes graphites such as natural graphite and artificial graphite, and carbon blacks such as acetylene black, Ketjen black, furnace black, channel black and thermal black. These conductive auxiliary agents may be used by appropriately mixing two or more thereof. The amount of the conductive auxiliary agents added is preferably 1 to 10 parts by mass to 100 parts by mass of the positive electrode active substance.

With respect to the average particle diameter of the positive electrode active substance, from the viewpoint of the reactivity with the electrolyte solution, the rate characteristics and the like, there can be used the positive electrode active substance having an average particle diameter, for example, in the range of 0.1 to 50 μm, preferably the positive electrode active substance having an average particle diameter in the range of 1 to 30 μm, and more preferably the positive electrode active substance having an average particle diameter in the range of 2 to 25 μm. Here, the average particle diameter means a particle diameter (median diameter: $D_{50}$) at a cumulative value of 50% in a particle size distribution (in terms of volume) by a laser diffraction scattering method.

The binder for the positive electrode is not especially limited, but polyvinylidene fluoride (PVDF), vinylidene fluoride-hexafluoropropylene copolymers, vinylidene fluoride-tetrafluoroethylene copolymers, styrene-butadiene copolymer rubber, polytetrafluoroethylene, polypropylene, polyethylene, polyimide or polyamideimide can be used, for example. Among these, from the viewpoint of versatility and low cost, polyvinylidene fluoride is preferable. The amount of the binder for the positive electrode to be used is, from the viewpoint of the binding force and the energy density, which are in a tradeoff relation, preferably 2 to 10 parts by mass to 100 parts by mass of the positive electrode active substance.

The positive electrode current collector is not especially limited, and there can optionally be used one usually used for common lithium ion secondary batteries. As the material of the positive electrode current collector, aluminum and stainless steel can be used, for example. The shape of the positive electrode current collector includes a foil shape, a flat plate shape and a mesh shape. As a suitable positive electrode current collector, there can be used an aluminum foil, a stainless steel-made lath board and the like.

A fabrication method of the positive electrode is such that the positive electrode can be fabricated, for example, by mixing the above positive electrode active substance, conductive auxiliary agent and binder, adding a solvent such as N-methylpyrrolidone and kneading the mixture to thereby prepare a slurry, applying the slurry on the current collector by a doctor blade method, a die coater method or the like, and then drying the resultant and as required, pressurizing the resultant.

<3. Negative Electrode>

As the negative electrode of the lithium ion secondary battery according to the exemplary embodiment, one in which a negative electrode active substance layer containing a negative electrode active substance and a binder is formed so as to cover on a negative electrode current collector can be used, for example. The binder binds the negative electrode active substance and the current collector, and the negative electrode active substances.

The negative electrode active substance includes lithium metal, metals or alloys alloyable with lithium, oxides capable of occluding and releasing lithium ions, and carbonaceous materials capable of occluding and releasing lithium ions.

Examples of the metal or alloy alloyable with lithium include elemental silicon, lithium-silicon alloys and lithium-tin alloys.

Examples of the oxide capable of occluding and releasing lithium ions include silicone oxide, niobium pentaoxide ($Nb_2O_5$), a lithium titanium composite oxide ($Li_{4/3}Ti_{5/3}O_4$) and titanium dioxide ($TiO_2$).

Further, examples of the carbonaceous material capable of occluding and releasing lithium ions include carbonaceous materials such as graphite materials (artificial graphite, natural graphite), carbon black (acetylene black, furnace black), coke, mesocarbon microbeads, hard carbon and graphite. Among these, in that the cycle characteristics and the safety are good and further the continuous charge characteristics are also excellent, use of the carbonaceous material is preferable. Here, the negative electrode active substance may be used singly or in any combination and ratio of two or more thereof.

Further from the point of the capacity, a negative electrode active substance containing silicon is preferable. Examples thereof include silicon and silicon compounds. Examples of the silicon include elemental silicon. Examples of the silicon compounds include silicon oxide, silicate salts, and compounds of a transition metal with silicon such as nickel silicide and cobalt silicide.

The silicon compound has a function of relaxing the expansion and contraction of the negative electrode active substance itself due to repeated charge and discharge, and is more preferable from the viewpoint of the charge and discharge cycle characteristics. Further, the silicon compound, depending on the kind of the silicon compound, has also a function of securing conduction between silicon regions. From these viewpoints, silicon oxide is preferable as the silicon compound.

The silicon oxide is not especially limited, but a silicon oxide represented by $SiO_x$ ($0<x\leq2$) can be used. The silicon oxide may contain Li; and as a silicon oxide containing Li, ne represented by $SiLi_yO_z$ ($y>0$, $2>z>0$) can be used, for example. Further, the silicon oxide may contain trace amounts of metal elements and nonmetal elements. The silicon oxide can contain, for example, 0.1 to 5% by mass of one or two or more elements selected from, for example, nitrogen, boron and sulfur. By making trace amounts of metal elements and nonmetal elements to be contained, the electric conduction of the silicon oxide can be improved. Further the silicon oxide may be crystalline or amorphous.

Further as the negative electrode active substance, more preferable is one containing a negative electrode active substance (preferably silicon or a silicon oxide) containing silicon, and a carbonaceous material capable of occluding and releasing lithium ions. The carbonaceous material can be contained also in the state of being composited with the negative electrode active substance (preferably silicon or a silicon oxide) containing silicon. The carbonaceous material, as in the case of the silicon oxide, has a function of relaxing the expansion and contraction of the negative electrode active substance itself due to repeated charge and discharge, and securing the conduction between silicon regions being the negative electrode active substance. Therefore, the coexistence of the negative electrode active substance (preferably silicon or a silicon oxide) containing silicon, and the carbonaceous material enables better cycle characteristics to be provided.

As the carbonaceous material, there can suitably be used graphite, amorphous carbon, diamond-like carbon, a carbon nanotube or a composite thereof. Here, the graphite, high in crystallinity, is high in electric conduction, and excellent in adhesiveness with the positive electrode current collector composed of a metal such as copper and in the voltage flatness. By contrast, the amorphous carbon, low in crystallinity, since being relatively small in the volume expansion, is large in an effect of relaxing the volume expansion of the negative electrode as a whole, and hardly causes the deterioration due to the heterogeneity such as crystal grain boundaries and defects. The content of the carbonaceous material in the negative electrode active substance is preferably made to be 2% by mass or more and 50% by mass or less, and more preferably made to be 2% by mass or more and 30% by mass or less.

A fabrication method of the negative electrode active substance containing silicon and a silicon compound includes the following method. In the case of using a silicon oxide as the silicon compound, examples of the fabrication method include a method in which elemental silicon and the silicon oxide are mixed, and sintered at a high temperature under reduced pressure. Further in the case of using a compound of a transition metal and silicon as the silicon compound, examples of the fabrication method include a method in which elemental silicon and the transition metal are mixed and melted, and a method in which the surface of elemental silicon is coated with the transition metal by vapor deposition or the like.

In the above-mentioned fabrication methods, the compositing further with carbon can also be combined. Examples of the compositing method include a method in which a mixed and sintered material of elemental silicon and a silicon compound is introduced in a gas atmosphere of an organic compound under a high-temperature non-oxygen atmosphere, and the organic compound is carbonized to form a coating layer composed of carbon, and a method in which a mixed and sintered material of elemental silicon and a silicon compound, and a precursor resin of carbon are mixed under a high-temperature non-oxygen atmosphere, and the precursor resin is carbonized to form a coating layer composed of carbon. Thus, there can be formed the coating layer composed of carbon on the periphery of a core composed of the elemental silicon and the silicon compound (for example, silicon oxide). Thereby, there can be attained the suppression of the volume expansion due to the charge and discharge and a further improving effect of the cycle characteristics.

In the case of using a negative electrode active substance containing silicon as the negative electrode active substance, preferable is a composite (hereinafter, referred to also as Si/SiO/C composite) containing silicon, a silicon oxide and a carbon material. Further, the whole or a part of the silicon oxide preferably has an amorphous structure. The silicon oxide having an amorphous structure can suppress the volume expansion of the carbonaceous material and silicon being other negative electrode active substances. This mechanism is not clear, but it is presumed that the fact that the silicon oxide has an amorphous structure has some effect on the formation of a coating at the interface of the carbonaceous material and the electrolyte solution. It is also conceivable that the amorphous structure relatively little develops the deterioration due to the heterogeneity such as crystal grain boundaries and defects. Here, the fact that the whole or a part of the silicon oxide has an amorphous structure can be checked by X-ray diffractometry (usual XRD measurement). Specifically, in the case where the silicon oxide has no amorphous structure, peaks characteristic of silicon oxide are observed; but, in the case where the whole or a part of the silicon oxide has an amorphous structure, the peaks characteristic of silicon oxide become broadened and the broadened peaks are observed.

In the Si/SiO/C composite, the whole or a part of silicon is preferably dispersed in the silicon oxide. By dispersing at least a part of the silicon in the silicon oxide, the volume expansion of the negative electrode as a whole can be more suppressed, and the decomposition of the electrolyte solution can also be suppressed. Here, the fact that the whole or a part of silicon is dispersed in the silicon oxide can be checked by using a transmission electron microscopic observation (usual TEM observation) and an energy dispersive X-ray spectroscopy (usual EDX measurement) in combination. Specifically, a cross-section of a sample is observed; and there is measured the oxygen concentration in moieties corresponding to silicon dispersed in the silicon oxide, and it can be confirmed that the silicon does not turns to an oxide.

In the Si/SiO/C composite, for example, the whole or a part of the silicon oxide has an amorphous structure and the whole or a part of the silicon is dispersed in the silicon oxide. Such a Si/SiO/C composite can be fabricated, for example, by a method disclosed in JP2004-47404A. That is, the Si/SiO/C composite can be obtained, for example, by subjecting a silicon oxide to a CVD process in an atmosphere containing an organic gas such as methane gas. The Si/SiO/C composite obtained by such a method has a form in which the surface of particles composed of the silicon oxide containing silicon is coated with carbon. Further, the silicon is nanoclustered in the silicon oxide.

In the Si/SiO/C composite, proportions of the silicon, the silicon oxide and the carbonaceous material are not especially limited. The silicon is, with respect to the Si/SiO/C composite, preferably made to be 5% by mass or more and 90% by mass or less, and more preferably made to be 20% by mass or more and 50% by mass or less. The silicon oxide is, with respect to the Si/SiO/C composite, preferably made to be 5% by mass or more and 90% by mass or less, and more preferably made to be 40% by mass or more and 70% by mass or less. The carbonaceous material is, with respect to the Si/SiO/C composite, preferably made to be 2% by mass or more and 50% by mass or less, and more preferably made to be 2% by mass or more and 30% by mass or less.

Further the Si/SiO/C composite may be a mixture of elemental silicon, the silicon oxide and the carbonaceous material, and can be fabricated also by mixing elemental silicon, the silicon oxide and the carbonaceous material by a mechanical milling. For example, the Si/SiO/C composite can be obtained by mixing elemental silicon, the silicon oxide and the carbonaceous material which are all particulate. For example, the Si/SiO/C composite can have such a constitution that the average particle diameter of the elemental silicon is smaller than the average particle diameter of the carbonaceous material and the average particle diameter of the silicon oxide. When such a constitution is made, since the particle diameter of the elemental silicon, which is large in the volume change involved in the charge and discharge, is relatively small, and the particle diameters of the carbonaceous material and the silicon oxide, which are small in the volume change, are relatively large, the formation of dendrite and the micropowdering of the alloy are more effectively suppressed. Further in the course of the charge and discharge, large-diameter particles and small-diameter particles alternately occlude and release lithium ions, whereby the generation of the residual stress and residual strain can be suppressed. The average particle diameter of the elemental silicon can be made to be, for example, 20 μm or less, and is preferably made to be 15 μm or less. The average particle diameter of the silicon oxide is preferably ½ or less of the average particle diameter of the carbonaceous material. The average particle diameter of the elemental silicon is preferably ½ or less of the average particle diameter of the silicon oxide. Further it is more preferable that the average particle diameter of the silicon oxide be ½ or less of the average particle diameter of the carbonaceous material, and the average particle diameter of the elemental silicon be ½ or less of the average particle diameter of the silicon oxide. When the average particle diameters are controlled in such ranges, the relaxing effect of the volume expansion can be attained more effectively and there can be obtained a secondary battery excellent in the balance among the energy density, the cycle life and the efficiency. More specifically, it is preferable that the average particle diameter of the silicon oxide be made to be ½ or less of the average particle diameter of the graphite and the average particle diameter of the elemental silicon be made to be ½ or less of the average particle diameter of the silicon oxide. Still more specifically, the average particle diameter of the elemental silicon can be made to be, for example, 20 μm or less, and is preferably made to be 15 μm or less.

The average particle diameter of the negative electrode active substance is, from the point that side reactions in the charge and discharge time are suppressed and the decrease in the charge and discharge efficiency is suppressed, preferably 1 μm or more, more preferably 2 μm or more, and still more preferably 5 μm or more, and from the viewpoint of the charge and discharge characteristics and from the viewpoint of the fabrication of the electrode (smoothness of the electrode surface, and the like), preferably 80 μm or less, and more preferably 40 μm or less. Here, the average particle diameter means a particle diameter (median diameter: $D_{50}$) at a cumulative value of 50% in the particle size distribution (in terms of volume) by a laser diffraction scattering method.

Further as the negative electrode active substance, there can also be used one in which the surface of the above-mentioned Si/SiO/C composite is treated with a silane coupling agent or the like.

The negative electrode active substance layer preferably contains as its main component the above-mentioned negative electrode active substance capable of occluding and releasing lithium ions; and specifically, the content of the negative electrode active substance is, with respect to the total of the negative electrode active substance layer containing the negative electrode active substance, the binder for the negative electrode and as required, various types of auxiliary agents and the like, preferably 55% by mass or more, and more preferably 65% by mass or more.

The binder for the negative electrode is not especially limited, but polyvinylidene fluoride, vinylidene fluoride-hexafluoropropylene copolymers, vinylidene fluoride-tetrafluoroethylene copolymers, styrene-butadiene copolymer rubber (SBR), polytetrafluoroethylene, polypropylene, polyethylene, polyimide and polyamideimide can be used, for example. Among these, from the viewpoint of the strong bindability, preferable are polyimide, polyamideimide, SBR, polyacrylic acid (including lithium salts, sodium salts and potassium salts neutralized with an alkali), and carboxymethyl cellulose (including lithium salts, sodium salts and potassium salts neutralized with an alkali). The amount of the binder for the negative electrode to be used is, from the viewpoint of the binding force and the energy density, which are in a tradeoff relation, preferably 5 to 25 parts by mass to 100 parts by mass of the negative electrode active substance.

The negative electrode current collector is not especially limited, and there can optionally be used one usually used for common lithium ion secondary batteries. As the material of the negative electrode current collector, a metallic material such as copper, nickel or SUS can be used, for example. Among these, copper is especially preferable from the point of ease of processing and cost. The negative electrode current collector is preferably previously subjected to a surface-roughening treatment. The shape of the negative electrode current collector includes a foil shape, a flat plate shape and a mesh shape. Further, there can also be used a perforated-type current collector such as an expanded metal or a punching metal.

A fabrication method of the negative electrode is such that the negative electrode can be produced, for example, as in the above-mentioned fabrication method of the positive electrode, by kneading a mixture of the above-mentioned negative electrode active substance and binder, and as required various types of auxiliary agents and the like, and a solvent to thereby prepare a slurry, applying the slurry on the current collector, then drying the resultant and as required, pressurizing the resultant.

<4. Separator>

The separator is not especially limited, but there can be used a monolayer or laminated porous film or non-woven fabric composed of a resin material of a polyolefin such as polypropylene or polyethylene, or the like. Further, a film in which a resin layer of a polyolefin or the like is coated or laminated with a dissimilar material can be used. Examples of such a film include one in which a polyolefin base material is coated with a fluorine compound or an inorganic microparticle, and one in which a polyolefin base material and an Aramid layer are laminated.

The thickness of the separator is, from the sides of the energy density of the battery and the mechanical strength of the separator, preferably 5 to 50 μm, and more preferably 10 to 40 μm.

<5. Structure of the Lithium Ion Secondary Battery>

The form of the lithium ion secondary battery is not especially limited, but includes coin-type batteries, button-type batteries, cylindrical batteries, rectangular batteries and laminate-type batteries.

For example, the laminate-type battery can be fabricated by alternately laminating the positive electrode, the separator and the negative electrode to form a laminate, connecting a metal terminal called a tab to the each electrode, putting the laminate in a container constituted of a laminate film being an outer package, and injecting the electrolyte solution and sealing the container.

The laminate film can appropriately be selected as long as being stable to the electrolyte solution and having a sufficient steam barrier property. As such a laminate film, a laminate film composed of a polyolefin (for example, polypropylene or polyethylene) coated with an inorganic material such as aluminum, silica or alumina can be used, for example. From the viewpoint of suppressing of the volume expansion, especially preferable is an aluminum laminate film composed of a polyolefin coated with aluminum.

The typical layer configuration of the laminate film includes a configuration in which a metal thin film layer and a thermally fusible resin layer are laminated. Further, another layer configuration of the laminate film includes a configuration in which on the surface on the opposite side to the thermally fusible resin layer of the metal thin film layer, a resin film (protective layer) composed of a polyester such as a polyethylene terephthalate or a polyamide such as nylon is further laminated. In the case where the container composed of the laminate film accommodating the laminate containing the positive electrode and the negative electrode is sealed, the container is so formed that the thermally fusible resin layer of the laminate film is made to face the resin layer itself, and can fuse with the thermally fusible resin layer itself on sealing portions. As the metal thin film layer of the laminate film, there is used, for example, a foil having a thickness of 10 to 100 μm of Al, Ti, a Ti alloy, Fe, stainless steel, a Mg alloy or the like. A resin to be used for the thermally fusible resin layer is not especially limited as long as being a resin capable of thermal fusion, but examples thereof include polypropylene, polyethylene, materials thereof modified with an acid, polyphenylene sulfide, polyester such as polyethylene terephthalate, polyamide, ethylene-vinyl acetate copolymers, and ionomer resins in which ethylene-methacrylic acid copolymers and ethylene-acrylic acid copolymers are intermolecularly bound through metal ions. The thickness of the thermally fusible resin layer is preferably 10 to 200 μm, and more preferably 30 to 100 μm.

Figure 1:
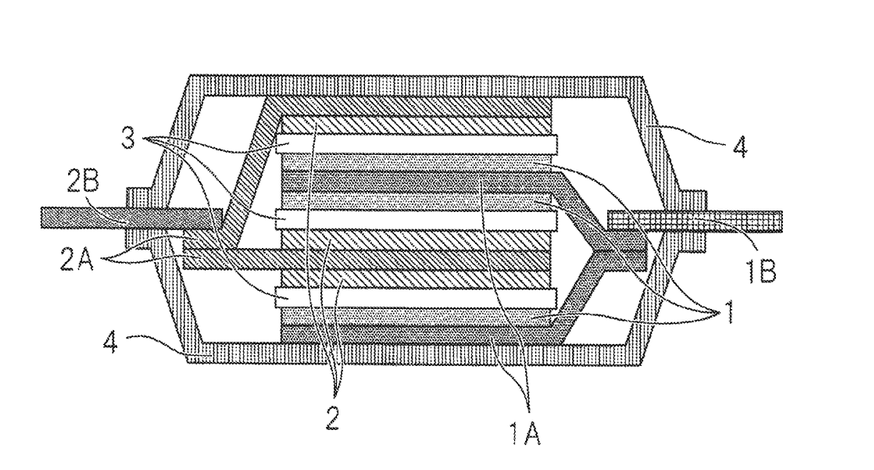
FIG. 1 is a cross-sectional view to interpret a constitution of a lithium ion secondary battery according to an exemplary embodiment.

FIG. 1 illustrates one example of a structure of a lithium ion secondary battery according to the exemplary embodiment.

Positive electrodes are constituted by forming positive electrode active substance layers 1 containing a positive electrode active substance on positive electrode current collectors 1A. As such positive electrodes, there are used a single-sided electrode in which the positive electrode active substance layer 1 is formed on one surface of the positive electrode current collector 1A, and a double-sided electrode in which the positive electrode active substance layer 1 is formed on each of both the surfaces of the positive electrode current collector 1A.

Negative electrodes are constituted by forming negative electrode active substance layers 2 containing a negative electrode active substance on negative electrode current collectors 2A. As such negative electrodes, there are used a single-sided electrode in which the negative electrode active substance layer 2 is formed on one surface of the negative electrode current collector 2A, and a double-sided electrode in which the negative electrode active substance layer 2 is formed on each of both the surfaces of the negative electrode current collector 2A.

These positive electrodes and negative electrodes are, as illustrated in FIG. 1, facingly arranged and laminated through separators 3. The two positive electrode current collectors 1A are mutually connected on one end-sides thereof, and a positive electrode tab 1B is connected to this connection portion. The two negative electrode current collectors 2A are mutually connected on the other end-sides thereof, and a negative electrode tab 2B is connected to this connection portion. A laminate (power generation element) containing the positive electrodes and the negative electrodes is accommodated in a container composed of outer packages (outer packaging laminate films) 4, and is in the state of being impregnated with an electrolyte solution. The positive electrode tab 1B and the negative electrode tab 2B are exposed outside the outer packages 4. Two sheets of rectangular laminate sheets are used as the outer packages 4, and overlaid so as to wrap the power generation element; and edge portions of four sides are sealed by fusion to thereby form the outer packaging container.

EXAMPLES

Hereinafter, Examples of the exemplary embodiment will be described.

Synthesis Example 1

Synthesis of a hydrofluoroether (HFE-1) in which in the formula (1), $R^1$ was a 2,2-difluoroethyl group.

[Formula 7]

2.269 g of potassium hydroxide was dispersed in 50 ml of tetrahydrofuran, and 3.084 g of 2,2-difluoroethanol was dropped under ice cooling. After 30 min, 10 g of perfluoropropoxyethylene was dropped, and the resulting mixture was stirred for 1 hour. Thereafter, the reaction mixture was stirred at room temperature for one night and injected in water; and an organic layer was washed with water until a water layer became neutral and thereafter dried with magnesium sulfate. The organic layer was filtered by a filter and distilled and refined to thereby obtain 9.29 g of a target hydrofluoroether (HFE-1) (colorless transparent liquid, boiling point: 33° C./25 mmHg, yield: 71%). The measurement result of the obtained hydrofluoroether (HFE-1) by $^1$H-NMR (CDCl$_3$) was as follows: δ were 5.94 (tt, 1H), 5.93 (dd, 1H) and 4.14 (dt, 2H).

Synthesis Example 2

Synthesis of a hydrofluoroether (HFE-2) in which in the formula (1), $R^1$ was a 2,2,3,3-tetrafluoropropyl group

[Formula 8]

A target hydrofluoroether (HFE-2) (colorless transparent liquid, boiling point: 46° C./25 mmHg, yield: 65%) was synthesized as in Synthesis Example 1, except for using 4.964 g of 2,2,3,3-tetrafluoro-1-propanol in place of using 3.084 g of 2,2-difluoroethanol used in Synthesis Example 1. The measurement result of the obtained hydrofluoroether (HFE-2) by $^1$H-NMR (CDCl$_3$) was as follows: δ were 5.95 (dt, 1H), 5.89 (tt, 1H) and 4.32 (t, 2H).

Synthesis Example 3

Synthesis of a hydrofluoroether (HFE-3) in which in the formula (1), $R^1$ was a 2,2,2-trifluoroethyl group

[Formula 9]

A target hydrofluoroether (HFE-3) (colorless transparent liquid, boiling point: 95 to 96° C., yield: 80%) was synthesized as in Synthesis Example 1, except for using 3.76 g of 2,2,2-trifluoroethanol in place of using 3.084 g of 2,2-difluoroethanol used in Synthesis Example 1. The measurement result of the obtained hydrofluoroether (HFE-3) by $^1$H-NMR (CDCl$_3$) was as follows: δ were 5.96 (dt, 1H) and 4.29 (q, 2H).

Synthesis Example 4

Synthesis of a hydrofluoroether (HFE-4) in which in the formula (1), $R^1$ was a 2,2,3,3,3-pentafluoropropyl group

[Formula 10]

A target hydrofluoroether (HFE-4) (colorless transparent liquid, yield: 80%) was synthesized as in Synthesis Example 1, except for using 5.64 g of 2,2,3,3,3-pentafluoro-1-propanol in place of using 3.084 g of 2,2-difluoroethanol used in Synthesis Example 1. The measurement result of the obtained hydrofluoroether HFE-4 by $^1$H-NMR (CDCl$_3$) was as follows: δ were 6.00 (dt, 1H) and 4.36 (q, 2H).

Synthesis Example 5

Synthesis of a hydrofluoroether (HFE-5) in which in the formula (1), R$^1$ was a 1,1,1,3,3,3-hexafluoroisopropyl group A target hydrofluoroether (HFE-5) (colorless transparent liquid, yield: 68%) was synthesized as in Synthesis Example 1, except for using 6.316 g of 1,1,1,3,3,3-hexafluoro-2-propanol in place of using 3.084 g of 2,2-difluoroethanol used in Synthesis Example 1. The measurement result of the obtained hydrofluoroether (HFE-5) by $^1$H-NMR (CDCl$_3$) was as follows: δ were 6.04 (dm, 1H) and 4.94 (sept, 1H).

Synthesis Example 6

Synthesis of a hydrofluoroether (HFE-8) in which in the formula (1), R$^1$ was a 2,2,3,3,4,4,4-heptafluorobutyl group A target hydrofluoroether (HFE-8) (colorless transparent liquid, yield: 56%) was synthesized as in Synthesis Example 1, except for using 7.46 g of 2,2,3,3,4,4,4-heptafluoro-1-butanol in place of using 3.084 g of 2,2-difluoroethanol used in Synthesis Example 1. The measurement result of the obtained hydrofluoroether (HFE-8) by $^1$H-NMR (CDCl$_3$) was as follows: δ were 5.95 (dt, 1H) and 4.40 (t, 2H).

Synthesis Example 7

Synthesis of a hydrofluoroether (HFE-9) in which in the formula (1), R$^1$ was 2,2,3,3,4,4,5,5-octafluoropentyl group A target hydrofluoroether (HFE-9) (colorless transparent liquid, boiling point: 66 to 67° C./25 mmHg, yield: 75%) was synthesized as in Synthesis Example 1, except for using 8.724 g of 2,2,3,3,4,4,5,5-octafluoropentanol in place of using 3.084 g of 2,2-difluoroethanol used in Synthesis Example 1. The measurement result of the obtained hydrofluoroether (HFE-9) by $^1$H-NMR (CDCl$_3$) was as follows: δ were 6.03 (tt, 1H), 5.95 (dt, 1H) and 4.4 (t, 2H).

Other Synthesis Examples

HFE-6 and HFE-7 could be synthesized, respectively, as in Example 1, by reactions of perfluoropropoxyethylene with alcohols (difluoromethanol and 2,2,3,3,4,4-hexafluoro-1-butanol) corresponding to "OR$^1$" in the formula (1).

Example 1

<Positive Electrode>

There was prepared a slurry containing 90% by mass of a lithium metal composite oxide Li$_{1.2}$Mn$_{0.4}$Ni$_{0.4}$O$_2$ as a positive electrode active substance, 5% by mass of Ketjen black as a conductive auxiliary agent, and 5% by mass of a polyvinylidene fluoride as a binder. The slurry was applied on a positive electrode current collector 1A composed of an aluminum foil (thickness: 20 μm), and dried to form a positive electrode active substance layer 1 of 175 μm in thickness to thereby obtain a single-sided electrode in which the positive electrode active substance layer was formed on one surface of the positive electrode current collector. The positive electrode active substance layer 1 was similarly formed on each of both surfaces of the positive electrode current collector 1A to thereby obtain a double-sided electrode in which the positive electrode active substance layer was formed on both the surfaces of the positive electrode current collector.

<Negative Electrode>

There was prepared a slurry containing 90% by mass of an artificial graphite of 15 μm in average particle diameter, 1% by mass of Ketjen black, and 9% by mass of a polyvinylidene fluoride. The slurry was applied on a negative electrode current collector 2A composed of a copper foil (thickness: 10 μm), and dried to form a negative electrode active substance layer 2 of 48 μm in thickness to thereby obtain a single-sided electrode in which the negative electrode active substance layer was formed on one surface of the negative electrode current collector. The negative electrode active substance layer 2 was similarly formed on each of both surfaces of the negative electrode current collector 2A to thereby obtain a double-sided electrode in which the negative electrode active substance layer was formed on both the surfaces of the negative electrode current collector.

<Nonaqueous Electrolyte Solution>

The hydrofluoroether (HFE-1) obtained in Synthesis Example 1, ethylene carbonate (EC) and diethyl carbonate (DEC) were mixed in a volume ratio (HFE-1/EC/DEC)=5/29/66, and LiPF$_6$ was dissolved therein so as to become 1.0 M (mol/L) to thereby prepare a nonaqueous electrolyte solution.

<Lithium Ion Secondary Battery>

The positive electrodes and the negative electrodes fabricated in the above methods were formed into predetermined shapes; thereafter, porous film separators 3 were interposed and laminated; and a positive electrode tab 1B and a negative electrode tab 2B were welded thereto, respectively, to thereby obtain a power generation element. The power generation element was wrapped in an outer package 4 composed of an aluminum laminate film; edge portions of three sides were thermally fused; and thereafter, the above nonaqueous electrolyte solution was injected, and impregnated under an appropriate degree of vacuum. Thereafter, the edge portion of the remaining side was sealed by thermal fusion under reduced pressure to thereby obtain a lithium ion secondary battery having a structure illustrated in FIG. 1 and before an activation treatment.

<Activation Treatment Step>

For the fabricated lithium ion secondary battery before an activation treatment, such cycles were twice repeated that charging was carried out at a current of 40 mA/g per the positive electrode active substance until 4.8 V; charging was further continued at a constant voltage of 4.8 V until the current became 5 mA/g; and thereafter discharging was carried out at a current of 40 mA/g per the positive electrode active substance until 2.0 V. Thereafter, the sealed portion was once broken to reduce the pressure to thereby let gases in the battery out; and sealing was again carried out to thereby obtain a lithium ion secondary battery according to the present Example.

Example 2

A lithium ion secondary battery was fabricated by the same method as in Example 1, except for replacing the hydrofluoroether (HFE-1) obtained in Synthesis Example 1 and used in Example 1 with the hydrofluoroether (HFE-2) obtained in Synthesis Example 2.

Example 3

A lithium ion secondary battery was fabricated by the same method as in Example 1, except for replacing the hydrofluoroether (HFE-1) obtained in Synthesis Example 1 and used in Example 1 with the hydrofluoroether (HFE-3) obtained in Synthesis Example 3.

Example 4

A lithium ion secondary battery was fabricated by the same method as in Example 1, except for replacing the hydrofluoroether (HFE-1) obtained in Synthesis Example 1 and used in Example 1 with the hydrofluoroether (HFE-4) obtained in Synthesis Example 4.

Example 5

A lithium ion secondary battery was fabricated by the same method as in Example 1, except for replacing the hydrofluoroether (HFE-1) obtained in Synthesis Example 1 and used in Example 1 with the hydrofluoroether (HFE-5) obtained in Synthesis Example 5.

Example 6

A lithium ion secondary battery was fabricated by the same method as in Example 1, except for replacing the hydrofluoroether (HFE-1) obtained in Synthesis Example 1 and used in Example 1 with the hydrofluoroether (HFE-8) obtained in Synthesis Example 6.

Example 7

A lithium ion secondary battery was fabricated by the same method as in Example 1, except for replacing the hydrofluoroether (HFE-1) obtained in Synthesis Example 1 and used in Example 1 with the hydrofluoroether (HFE-9) obtained in Synthesis Example 7.

Example 8

A lithium ion secondary battery was fabricated by the same method as in Example 1, except for altering the positive electrode active substance ($Li_{1.2}Mn_{0.4}Ni_{0.4}O_2$) used in Example 1 to $Li_{1.19}Mn_{0.52}Fe_{0.22}O_{1.98}$.

Example 9

A lithium ion secondary battery was fabricated by the same method as in Example 1, except for altering the positive electrode active substance ($Li_{1.2}Mn_{0.4}Ni_{0.4}O_2$) used in Example 1 to $Li_{1.21}Mn_{0.46}Fe_{0.15}Ni_{0.15}O_{2.0}$.

Example 10

A lithium ion secondary battery was fabricated by the same method as in Example 1, except for altering the solvent composition of the nonaqueous electrolyte solution used in Example 1 to that in a volume ratio (HFE-1/EC/DEC)=20/30/50.

Example 11

A lithium ion secondary battery was fabricated by the same method as in Example 10, except for replacing the hydrofluoroether (HFE-1) used in Example 10 with the hydrofluoroether HFE-2 obtained in Synthesis Example 2.

Example 12

A lithium ion secondary battery was fabricated by the same method as in Example 10, except for replacing the hydrofluoroether (HFE-1) used in Example 10 with the hydrofluoroether (HFE-9) obtained in Synthesis Example 7 and replacing DEC used in Example 10 with EMC. Here, EMC means ethyl methyl carbonate.

Example 13

A lithium ion secondary battery was fabricated by the same method as in Example 1, except for altering the solvent composition of the nonaqueous electrolyte solution used in Example 1 to HFE-1/EC/DEC/FEC=20/30/45/5 (in volume ratio). Here, FEC means fluoroethylene carbonate.

Example 14

A lithium ion secondary battery was fabricated by the same method as in Example 13, except for replacing FEC used in Example 13 with 1,1,2,2-tetrafluoroethyl 2,2,3,3-tetrafluoropropyl ether (FE-1).

Example 15

A lithium ion secondary battery was fabricated by the same method as in Example 13, except for replacing FEC used in Example 13 with tris(2,2,2-trifluoroethyl) phosphate (TFP).

Example 16

A lithium ion secondary battery was fabricated by the same method as in Example 1, except for altering the solvent composition of the nonaqueous electrolyte solution used in Example 1 to HFE-1/EC/EMC=50/10/40 (in volume ratio). Here, EMC means ethyl methyl carbonate.

Example 17

A lithium ion secondary battery was fabricated by the same method as in Example 1, except for altering the solvent composition of the nonaqueous electrolyte solution used in Example 1 to HFE-2/EC/EMC=50/10/40 (in volume ratio).

Comparative Example 1

A lithium ion secondary battery was fabricated by the same method as in Example 1, except for altering the solvent composition of the nonaqueous electrolyte solution used in Example 1 to a composition, containing no hydrofluoroether represented by the general formula (1), of EC/DEC=30/70 (in volume ratio).

Comparative Example 2

A lithium ion secondary battery was fabricated by the same method as in Example 8, except for altering the solvent composition of the nonaqueous electrolyte solution used in Example 8 to a composition, containing no hydrofluoroether represented by the general formula (1), of EC/DEC=30/70 (in volume ratio).

Comparative Example 3

A lithium ion secondary battery was fabricated by the same method as in Example 9, except for altering the solvent composition of the nonaqueous electrolyte solution used in Example 9 to a composition, containing no hydrofluoroether represented by the general formula (1), of EC/DEC=30/70 (in volume ratio).

Comparative Example 4

A lithium ion secondary battery was fabricated by the same method as in Example 10, except for replacing the hydrofluoroether (HFE-1) used in Example 10 with a fluorine-containing ether of diether type having the following structure (FE-2) (1,2-(1,1,2,2-tetrafluoroethoxy)ethane).

[Formula 14]

$$CHF_2CF_2OCH_2CH_2OCF_2CHF_2 \qquad FE\text{-}2$$

<Evaluation Methods of the Lithium Ion Secondary Batteries>

For the lithium ion secondary batteries fabricated in the above Examples and Comparative Examples, charging was carried out in a thermostatic chamber at 45° C. at a constant current of 40 mA/g until 4.8 V, and charging was further continued at a constant voltage of 4.8 V until the current became 5 mA/g. Thereafter, discharging was carried out at a current of 5 mA/g until 2.0 V, and the initial capacity was determined. Further for the lithium ion secondary batteries after the initial capacities were measured, such charge and discharge cycles were 30 times repeated that charging was carried out in a thermostatic chamber at 45° C. at a constant current of 40 mA/g until 4.8 V; charging was further continued at a constant voltage of 4.8 V until the current became 5 mA/g; thereafter, discharging was carried out at a current of 40 mA/g until 2.0 V. The capacity retention rates after the 30 cycles were determined from ratios of discharge capacities obtained at the 30th cycle to initial capacities obtained at the first cycle. Further the amounts of gas generated after the 30 cycles were determined with the amount of gas generated of Comparative Example 1 being taken as 100. The amounts of gas generated were measured by an Archimedes method.

<Evaluation Results of the Lithium Ion Secondary Batteries>

There are collectively shown in Table 2 the solvent compositions in the nonaqueous electrolyte solutions and the positive electrode materials used in the Examples and the Comparative Examples, and the capacity retention rates after the 30 cycles and the amounts of gas generated after the 30 cycles obtained by the above evaluation methods.

Comparing the Examples with the Comparative Examples, it has been found that by using the nonaqueous electrolyte solutions containing a hydrofluoroether of diether type of the present Examples, the amounts of gas generated in the cycle time of the lithium ion secondary batteries could be reduced and high capacity retention rates could stably be attained.

TABLE 2

|  | Solvent Composition in Nonaqueous Electrolyte Solution | Positive Electrode Material | Capacity Retention Rate | Amount of Gas Generated[1)] |
|---|---|---|---|---|
| Example 1 | HFE-1/EC/DEC = 5/29/66 | $Li_{1.2}Mn_{0.4}Ni_{0.4}O_2$ | 72% | 65 |
| Example 2 | HFE-2/EC/DEC = 5/29/66 | $Li_{1.2}Mn_{0.4}Ni_{0.4}O_2$ | 78% | 64 |
| Example 3 | HFE-3/EC/DEC = 5/29/66 | $Li_{1.2}Mn_{0.4}Ni_{0.4}O_2$ | 80% | 60 |
| Example 4 | HFE-4/EC/DEC = 5/29/66 | $Li_{1.2}Mn_{0.4}Ni_{0.4}O_2$ | 81% | 60 |
| Example 5 | HFE-5/EC/DEC = 5/29/66 | $Li_{1.2}Mn_{0.4}Ni_{0.4}O_2$ | 73 | 65 |
| Example 6 | HFE-8/EC/DEC = 5/29/66 | $Li_{1.2}Mn_{0.4}Ni_{0.4}O_2$ | 77 | 63 |
| Example 7 | HFE-9/EC/DEC = 5/29/66 | $Li_{1.2}Mn_{0.4}Ni_{0.4}O_2$ | 80 | 61 |
| Example 8 | HFE-1/EC/DEC = 5/29/66 | $Li_{1.19}Mn_{0.52}Fe_{0.22}O_{1.98}$ | 65% | 75 |
| Example 9 | HFE-1/EC/DEC = 5/29/66 | $Li_{1.21}Mn_{0.46}Fe_{0.15}Ni_{0.15}O_{2.0}$ | 66% | 72 |
| Example 10 | HFE-1/EC/DEC = 20/30/50 | $Li_{1.2}Mn_{0.4}Ni_{0.4}O_2$ | 82% | 60 |
| Example 11 | HFE-2/EC/DEC = 20/30/50 | $Li_{1.2}Mn_{0.4}Ni_{0.4}O_2$ | 83% | 58 |
| Example 12 | HFE-9/EC/EMC = 20/30/50 | $Li_{1.2}Mn_{0.4}Ni_{0.4}O_2$ | 81% | 56 |

TABLE 2-continued

| | Solvent Composition in Nonaqueous Electrolyte Solution | Positive Electrode Material | Capacity Retention Rate | Amount of Gas Generated[1] |
|---|---|---|---|---|
| Example 13 | HFE-1/EC/DEC/FEC = 20/30/45/5 | $Li_{1.2}Mn_{0.4}Ni_{0.4}O_2$ | 83% | 58 |
| Example 14 | HFE-1/EC/DEC/FE-1 = 20/30/45/5 | $Li_{1.2}Mn_{0.4}Ni_{0.4}O_2$ | 82% | 59 |
| Example 15 | HFE-1/EC/DEC/TFP = 20/30/45/5 | $Li_{1.2}Mn_{0.4}Ni_{0.4}O_2$ | 82% | 58 |
| Example 16 | HFE-1/EC/EMC = 50/10/40 | $Li_{1.2}Mn_{0.4}Ni_{0.4}O_2$ | 80% | 52 |
| Example 17 | HFE-2/EC/EMC = 50/10/40 | $Li_{1.2}Mn_{0.4}Ni_{0.4}O_2$ | 81% | 50 |
| Comparative Example 1 | EC/DEC = 30/70 | $Li_{1.2}Mn_{0.4}Ni_{0.4}O_2$ | 44% | 100 |
| Comparative Example 2 | EC/DEC = 30/70 | $Li_{1.19}Mn_{0.52}Fe_{0.22}O_{1.98}$ | 26% | 128 |
| Comparative Example 3 | EC/DEC = 30/70 | $Li_{1.21}Mn_{0.46}Fe_{0.15}Ni_{0.15}O_{2.0}$ | 30% | 120 |
| Comparative Example 4 | FE-2/EC/DEC = 20/30/50 | $Li_{1.2}Mn_{0.4}Ni_{0.4}O_2$ | 75% | 92 |

[1] amount of gas generated: a relative value with the amount of gas generated of Comparative Example 1 being taken as 100

In the foregoing, the present invention has been described with reference to the exemplary embodiments and Examples; however, the present invention is not limited to the above exemplary embodiments and Examples. Various modifications understandable to those skilled in the art may be made to the constitution and details of the present invention within the scope thereof.

INDUSTRIAL APPLICABILITY

The lithium ion secondary battery using a nonaqueous electrolyte solution containing a hydrofluoroether of diether type according to the exemplary embodiments, since being capable of suppressing the gas generation in the cycle time and exhibiting excellent characteristics, can suitably be utilized, for example, in all sorts of industrial fields needing power sources and industrial fields related to transport, storage and supply of the electric energy. Specifically, the lithium ion secondary battery can be utilized for power sources of mobile devices such as cell phones, laptop computers, tablet terminals and portable game machines; power sources of travel and transportation media such as electric cars, hybrid cars, motorcycles and electrically assisted bicycles; household power storage systems; backup power sources such as UPS; power storage facilities storing power generated by solar light power generation and wind power generation; and the like.

The present application claims the right of priority based on Japanese Patent Application No. 2015-062654, filed on Mar. 25, 2015, the entire disclosure of which is incorporated herein by reference.

REFERENCE SIGNS LIST

1: POSITIVE ELECTRODE ACTIVE SUBSTANCE LAYER
1A: POSITIVE ELECTRODE CURRENT COLLECTOR
1B: POSITIVE ELECTRODE TAB
2: NEGATIVE ELECTRODE ACTIVE SUBSTANCE LAYER
2A: NEGATIVE ELECTRODE CURRENT COLLECTOR
2B: NEGATIVE ELECTRODE TAB
3: SEPARATOR
4: OUTER PACKAGE (LAMINATE OUTER PACKAGING FILM)

The invention claimed is:

1. A nonaqueous electrolyte solution for a lithium ion secondary battery, comprising:
an electrolytic salt; and
a hydrofluoroether compound represented by the following formula (1):

[Formula 1]

$$CF_3CF_2CF_2OCHFCF_2OR^1 \qquad (1)$$

wherein $R^1$ represents a difluoromethyl group, a 2,2-difluoroethyl group, a 2,2,2-trifluoroethyl group, a 2,2,3,3,3-pentafluoropropyl group, a 2,2,3,3-tetrafluoropropyl group, a 1,1,1,3,3,3-hexafluoroisopropyl group, a 2,2,3,3,4,4,4-heptafluorobutyl group, a 2,2,3,3,4,4-hexafluorobutyl group, or a 2,2,3,3,4,4,5,5-octafluoropentyl group.

2. The nonaqueous electrolyte solution according to claim 1, further comprising at least one of a chain carbonate and a cyclic carbonate.

3. The nonaqueous electrolyte solution according to claim 2, wherein the chain carbonate is at least one compound selected from the group consisting of dimethyl carbonate, diethyl carbonate, ethyl methyl carbonate, dipropyl carbonate, dibutyl carbonate, methyl propyl carbonate, methyl isopropyl carbonate, methyl butyl carbonate, fluoromethyl methyl carbonate, 2-fluoroethyl methyl carbonate, ethyl-(2-fluoroethyl) carbonate, ethyl-(2,2-difluoroethyl) carbonate, bis(2-fluoroethyl) carbonate and ethyl-(2,2,2-trifluoroethyl) carbonate; and
the cyclic carbonate is at least one compound selected from the group consisting of ethylene carbonate, propylene carbonate, fluoroethylene carbonate, butyl ene carbonate, vinylene carbonate and vinyl ethylene carbonate.

4. The nonaqueous electrolyte solution according to claim 1, comprising a cyclic carbonate.

5. The nonaqueous electrolyte solution according to claim 1, further comprising at least one of a fluorine-containing ether represented by the following formula (2) and a fluorine-containing phosphate ester represented by the following formula (3):

[Formula 2]

$$R^2-O-R^3 \qquad (2)$$

wherein $R^2$ and $R^3$ are each independently an alkyl group or a fluorine-containing alkyl group, and at least one of $R^2$ and $R^3$ is a fluorine-containing alkyl group, and

[Formula 3]

(3)

wherein $R^4$, $R^5$ and $R^6$ are each independently an alkyl group or a fluorine-containing alkyl group, and at least one of $R^4$, $R^5$ and $R^6$ is a fluorine-containing alkyl group.

6. The nonaqueous electrolyte solution according to claim 1, wherein a content of the hydrofluoroether compound represented by the formula (1) is 1% by volume to 60% by volume with respect to the whole of nonaqueous solvents in the nonaqueous electrolyte solution.

7. A lithium ion secondary battery, comprising a positive electrode containing a positive electrode active substance material capable of occluding and releasing lithium ions, a negative electrode containing a negative electrode active substance material capable of occluding and releasing lithium ions, and a nonaqueous electrolyte solution, wherein the nonaqueous electrolyte solution is the nonaqueous electrolyte solution according to claim 1.

8. The lithium ion secondary battery according to claim 7, wherein the positive electrode active substance material comprises a lithium metal composite oxide.

9. The lithium ion secondary battery according to claim 7, wherein the negative electrode active substance material comprises at least one of elemental silicon, silicon oxides and a carbonaceous material.

10. The nonaqueous electrolyte solution according to claim 1, wherein the electrolytic salt comprises a lithium salt.

11. The nonaqueous electrolyte solution according to claim 1, wherein the electrolytic salt comprises at least one selected from the group consisting of $LiPF_6$, $LiBF_4$, $LiN(SO_2F)_2$, $LiN(SO_2CF_3)_2$ and $LiN(SO_2C_2F_5)_2$.

12. A hydrofluoroether compound, represented by the following formula (1):

[Formula 4]

(1)

wherein $R^1$ represents a difluoromethyl group, a 2,2-difluoroethyl group, a 2,2,3,3,3-pentafluoropropyl group, a 2,2,3,3-tetrafluoropropyl group, a 1,1,1,3,3,3-hexafluoroisopropyl group, a 2,2,3,3,4,4,4-heptafluorobutyl group, a 2,2,3,3,4,4-hexafluorobutyl group, or a 2,2,3,3,4,4,5,5-octafluoropentyl group.

* * * * *